US009839221B2

(12) United States Patent
Suzuki et al.

(10) Patent No.: US 9,839,221 B2
(45) Date of Patent: Dec. 12, 2017

(54) AGENT FOR IMPARTING ANTI-BACTERIAL/ANTI-FUNGAL PROPERTIES, FIBER PROCESSING AGENT, AND PRODUCTION METHOD FOR ANTI-BACTERIAL/ANTI-FUNGAL FIBER

(75) Inventors: Kimio Suzuki, Osaka (JP); Osamu Goushi, Osaka (JP)

(73) Assignee: OSAKA KASEI CO., LTD., Osaka (JP)

(*) Notice: Subject to any disclaimer, the term of this patent is extended or adjusted under 35 U.S.C. 154(b) by 0 days.

(21) Appl. No.: 14/352,229

(22) PCT Filed: Aug. 10, 2012

(86) PCT No.: PCT/JP2012/070516
§ 371 (c)(1),
(2), (4) Date: Apr. 16, 2014

(87) PCT Pub. No.: WO2013/058008
PCT Pub. Date: Apr. 25, 2013

(65) Prior Publication Data
US 2014/0272152 A1    Sep. 18, 2014

(30) Foreign Application Priority Data
Oct. 18, 2011  (JP) ................................. 2011-228898

(51) Int. Cl.
| | | |
|---|---|---|
| *A01N 55/02* | (2006.01) | |
| *A01N 43/40* | (2006.01) | |
| *D06M 13/355* | (2006.01) | |
| *D06M 15/03* | (2006.01) | |
| *A01N 25/34* | (2006.01) | |
| *A01N 43/16* | (2006.01) | |
| *A01N 59/16* | (2006.01) | |
| *D06M 15/05* | (2006.01) | |
| *D06M 15/07* | (2006.01) | |
| *D06M 15/09* | (2006.01) | |
| *D06M 15/53* | (2006.01) | |
| *D06M 16/00* | (2006.01) | |

(52) U.S. Cl.
CPC ............ *A01N 55/02* (2013.01); *A01N 25/34* (2013.01); *A01N 43/16* (2013.01); *A01N 43/40* (2013.01); *A01N 59/16* (2013.01); *D06M 13/355* (2013.01); *D06M 15/03* (2013.01); *D06M 15/05* (2013.01); *D06M 15/07* (2013.01); *D06M 15/09* (2013.01); *D06M 15/53* (2013.01); *D06M 16/00* (2013.01); *A01N 2300/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,785,985 A | * | 1/1974 | Grand | A01N 43/40 510/124 |
| 3,817,762 A | * | 6/1974 | Brake | C09D 5/14 106/18.32 |
| 5,342,437 A | * | 8/1994 | Gavin | C09D 5/1612 106/16 |
| 5,458,906 A | * | 10/1995 | Liang | A01N 25/34 427/2.31 |
| 5,540,920 A | * | 7/1996 | Vinopal | A01N 43/40 424/405 |
| 5,614,538 A | * | 3/1997 | Nelson, Jr. | A01N 43/40 106/18.33 |
| 5,854,266 A | * | 12/1998 | Nelson, Jr. | 514/345 |
| 5,888,526 A | * | 3/1999 | Tsubai | A01N 25/34 424/402 |
| 6,344,207 B1 | | 2/2002 | Goto et al. | |
| 7,026,308 B1 | | 4/2006 | Gavin et al. | |
| 7,455,851 B1 | | 11/2008 | Nelson et al. | |
| 2002/0018794 A1 | * | 2/2002 | Goto | A01N 25/34 424/404 |
| 2004/0253194 A1 | | 12/2004 | Rioux et al. | |

(Continued)

FOREIGN PATENT DOCUMENTS

| | | |
|---|---|---|
| CA | 2 466 781 | 6/2003 |
| CN | 1364056 | 8/2002 |

(Continued)

OTHER PUBLICATIONS

Definitions of surfactant/surface active agent and wetting agent on pp. 1108, 1109 and 1227 of Hawley's Condensed Chemical Dictionary, 12$^{th}$ Edition, 1993.*
Caplus/wpix/japio abstracts and machine translation and original patent of JP 2001-288017, Oct. 2001.*
CAS Registry file for RN 13463-41-7, Nov. 1984.*
Caplus/ wpix/japio abstracts and machine translation and original patent of JP 2006-001852, Jan. 2006.*
International Search Report dated Oct. 2, 2012 in International (PCT) Application No. PCT/JP2012/070516.
International Preliminary Report on Patentability dated Apr. 22, 2014 and English translation of Written Opinion of the International Searching Authority dated Oct. 2, 2012 in International (PCT) Application No. PCT/JP2012/070516.

(Continued)

*Primary Examiner* — Erma Cameron
(74) *Attorney, Agent, or Firm* — Wenderoth, Lind & Ponack, L.L.P.

(57) ABSTRACT

An object of the present invention is to make it possible that a pyridine antibacterial/antifungal agent is dispersed stably in a liquid for appropriate impartation of the pyridine antibacterial/antifungal agent to fibers, and that when fibers are processed with the agent which is mixed with various other treating agents such as dyes and softeners, there is no negative influences on the process of the fibers for imparting antibacterial/antifungal properties. An antibacterial/antifungal properties-imparting agent contains a pyridine antibacterial/antifungal agent; a modified polysaccharide having reduced hydroxyl groups; and a wetting agent; but does not contain a surfactant. After applying the antibacterial/antifungal properties-imparting agent to fibers, the fibers undergo a heating process.

9 Claims, No Drawings

(56) References Cited

U.S. PATENT DOCUMENTS

| | | |
|---|---|---|
| 2005/0020468 A1 | 1/2005 | Frantz et al. |
| 2005/0101487 A1* | 5/2005 | Beilfuss ............... A01N 43/70 504/134 |
| 2005/0158263 A1 | 7/2005 | Rioux et al. |
| 2005/0191270 A1 | 9/2005 | Gruening et al. |
| 2006/0198814 A1* | 9/2006 | Gruening et al. ........... 424/78.3 |
| 2006/0222615 A1 | 10/2006 | Kuroda et al. |
| 2006/0246097 A1* | 11/2006 | Hidaka ........................ 424/401 |
| 2006/0257441 A1* | 11/2006 | Komai ................... A01N 65/20 424/405 |
| 2007/0117895 A1* | 5/2007 | Lei ....................... C08K 5/0008 524/287 |
| 2007/0248561 A1 | 10/2007 | Milbradt et al. |
| 2007/0293800 A1* | 12/2007 | McMaken et al. .............. 602/48 |
| 2008/0233062 A1* | 9/2008 | Krishnan ......................... 424/59 |
| 2009/0047851 A1 | 2/2009 | Nelson et al. |
| 2009/0130161 A1* | 5/2009 | Sarangapani .................. 424/409 |
| 2009/0221463 A1* | 9/2009 | Kitko et al. ................... 510/120 |
| 2010/0087395 A1 | 4/2010 | Kuroda et al. |
| 2011/0070275 A1* | 3/2011 | Hidaka ........................ 424/401 |
| 2011/0245191 A1 | 10/2011 | Rosentel, Jr. et al. |
| 2012/0251627 A1 | 10/2012 | Nelson et al. |
| 2015/0011137 A1* | 1/2015 | Kollner ................... A47K 3/38 442/83 |

FOREIGN PATENT DOCUMENTS

| | | |
|---|---|---|
| CN | 1651640 | 8/2005 |
| EP | 1 607 081 | 12/2005 |
| EP | 1 847 253 | 10/2007 |
| JP | 3-34904 | 2/1991 |
| JP | 11-335202 | 12/1999 |
| JP | 2000-8275 | 1/2000 |
| JP | 2000-119960 | 4/2000 |
| JP | 2001-288014 | 10/2001 |
| JP | 2001-288015 | 10/2001 |
| JP | 2001-288017 | 10/2001 |
| JP | 2002-105855 | 4/2002 |
| JP | 2007-126778 | 5/2007 |
| JP | 2012-1868 | 1/2012 |
| WO | 2006/038631 | 4/2006 |
| WO | 2011/071805 | 6/2011 |

OTHER PUBLICATIONS

Office Action dated Mar. 18, 2015 in corresponding Chinese Application No. 201280051073.2, with partial English translation.
European Search Report dated Jul. 24, 2015 in corresponding European Patent Application No. 12841238.4.

* cited by examiner

AGENT FOR IMPARTING ANTI-BACTERIAL/ANTI-FUNGAL PROPERTIES, FIBER PROCESSING AGENT, AND PRODUCTION METHOD FOR ANTI-BACTERIAL/ANTI-FUNGAL FIBER

TECHNICAL FIELD

The present invention relates to antibacterial/antifungal properties-imparting agents, fiber processing agents and methods for producing antibacterial/antifungal fibers. The present invention relates particularly to imparting antibacterial/antifungal properties to, e.g., fibers, with a pyridine antibacterial/antifungal agent, and is characteristic in that this pyridine antibacterial/antifungal agent is dispersed stably in a liquid for appropriate impartation of the pyridine antibacterial/antifungal agent, and that when fibers are processed with the agent which is mixed with various other treating agent such as dyes and softeners, the invention prevents the antibacterial/antifungal properties-imparting agent from forming aggregation and foaming, making it possible to appropriately carry out processing of fibers for imparting antibacterial/antifungal properties together with other processes.

BACKGROUND ART

There has been increasing demand for hygienic quality in fiber products such as clothing, duvet covers, curtains, towels, wall cloth (wallpaper), etc. In response to this, various fiber products are now treated with antibacterial/antifungal properties-imparting processes. Particularly in recent years, in-hospital infection and the like are considered to be increasing threats to health, and there have been considerable interests in developing antibacterial/antifungal properties-imparting technique for surgical gowns and various other fiber products which are used in medical facilities.

Thus far, fiber products made of synthetic fibers for example, have their antibacterial/antifungal properties imparted commonly by: mixing a chemical agent such as an antibacterial/antifungal agent, with a spinning dope; spinning the dope thereby producing an antibacterial/antifungal fiber; and then making an antibacterial/antifungal yarn/thread by using the fiber individually or by blending it with other fibers, to obtain fiber merchandise which possesses antibacterial/antifungal properties. Another common practice is first manufacturing a fiber whether it is a fiber itself or a fiber product; and then applying chemical agents such as an antibacterial/antifungal agent to the fiber to impart antibacterial/antifungal properties.

A problem, however, with the above-described process of mixing chemical agents such as an antibacterial/antifungal agent with a spinning dope and spinning the dope, is that during the fiber spinning process, the chemical agents, e.g., the antibacterial agent and/or antifungal agent precipitate on nozzle surfaces, causing yarn-making troubles such as frequent breakage of filament.

On the other hand, in the case where chemical agents such as antibacterial/antifungal agents are applied to a fiber, i.e., a fiber or a fiber product, thereby imparting antibacterial/antifungal properties later to the fiber, wash durability is not always adequate. Especially with repeated cycles of industrial laundry in which washing is commonly performed at 60 through 85 degrees Celsius, there has been a problem that these fibers show drastic deterioration in their antibacterial/antifungal properties.

In recent years, there have been proposals for use of pyridine antibacterial/antifungal agents such as zinc pyrithione, for their superior wash durability as disclosed in Patent Literature 1 through 4.

In cases where a pyridine antibacterial/antifungal agent such as zinc pyrithione is applied to fibers to impart antibacterial/antifungal properties to the fibers, a common process is that the antibacterial/antifungal agent in the form of powder is dispersed in a liquid such as water to make a dispersion liquid in which the antibacterial/antifungal agent is dispersed, and then application to the fibers is made in this dispersion liquid because pyridine antibacterial/antifungal agents are barely soluble in solvents such as water.

In performing this process of applying a pyridine antibacterial/antifungal agent to fibers in a dispersion liquid where the agent is dispersed, it is a common practice that a surfactant of various types, such as anionic, cationic and nonionic surfactants, is added in order to maintain a state of stable dispersion of the pyridine antibacterial/antifungal agent in the liquid.

It is also a common practice that when imparting antibacterial/antifungal properties, etc. to fibers by applying an pyridine antibacterial/antifungal agent dispersion liquid to the fibers as described above, various treating agents such as dyes and softeners are used together with the dispersion liquid in which the antibacterial/antifungal agent is dispersed, for a purpose of performing several treatments in a single process.

Here is a problem, however, that if a dispersion liquid which contains a pyridine antibacterial/antifungal agent dispersed therein as described above and an anionic surfactant added thereto is used together with a treating agent containing cations, or if a dispersion liquid containing a cationic surfactant is used together with a treating agent containing anions, then they react chemically with each other to form aggregation, making it impossible to appropriately disperse the pyridine antibacterial/antifungal agent. This means that if an anionic or cationic surfactant is used, types of usable treating agents will be limited, which in turn makes it impossible to use an appropriate treating agent in performing a process. Also, if an antibacterial/antifungal properties-imparting process is performed separately from other processes, then it will lead to an increased number of process steps, resulting in increased cost.

Further, there have been other problems. For example, when a surfactant of various types such as anionic, cationic, nonionic, etc. is added to a dispersion liquid in which a pyridine antibacterial/antifungal agent is dispersed, foaming can occur, making it impossible to appropriately apply pyridine antibacterial/antifungal agent to fibers.

CITATION LIST

Patent Literature

Patent Literature 1: JP-A-2000-8275
Patent Literature 2: JP-A-2001-288014
Patent Literature 3: JP-A-2001-288015
Patent Literature 4: JP-A-H11-335202

SUMMARY OF INVENTION

Technical Problem

An object of the present invention is to make it possible that when, for example, imparting antibacterial/antifungal properties to fibers with a pyridine antibacterial/antifungal agent as described above, the pyridine antibacterial/antifungal agent is dispersed stably in a liquid for appropriate impartation of the pyridine antibacterial/antifungal agent to the fibers, and that when fibers are processed with the agent which is mixed with various other treating agents such as dyes and softeners, the antibacterial/antifungal properties-imparting agent will not form aggregation nor foaming, keeping it possible that the processing of the fibers for imparting antibacterial/antifungal properties can be appropriately carried out together with other processes.

Solution to Problem

In order to solve the problems described above, the present invention provides an antibacterial/antifungal properties-imparting agent which contains: a pyridine antibacterial/antifungal agent; a modified polysaccharide having reduced hydroxyl groups; and a wetting agent; but does not contain a surfactant.

The present invention also provides a fiber processing agent which contains the antibacterial/antifungal properties-imparting agent as described above.

Further, the present invention provides a method for producing antibacterial/antifungal fibers which includes steps of: applying one of the antibacterial/antifungal properties-imparting agents described above to a fiber; and thereafter heating the fiber.

Advantageous Effects of Invention

According to the antibacterial/antifungal properties-imparting agent offered by the present invention, as has been described above, the agent contains a pyridine antibacterial/antifungal agent; a modified polysaccharide having reduced hydroxyl groups; and a wetting agent. But on the other hand, the agent does not contain any surfactant. Therefore, when dispersing the pyridine antibacterial/antifungal agent in a liquid such as water, even if an amount of the pyridine antibacterial/antifungal agent is increased, the pyridine antibacterial/antifungal agent is dispersed stably in the liquid due to the modified polysaccharide which has reduced number of hydroxyl groups, and due to the wetting agent as well. Further, even if a dye, a softener or other treating agents contain cations or anions like in the above-described cases where an anionic or a cationic surfactant is added, there is no chemical reactions, so there is no aggregation, and therefore the pyridine antibacterial/antifungal agent is kept appropriately dispersed. Still further, there is no foaming unlike in the cases where a surfactant of various types such as anionic, cationic or nonionic types is added.

Hence, it is now possible to appropriately apply the pyridine antibacterial/antifungal agent to fibers using the antibacterial/antifungal properties-imparting agent which is a liquid in which the pyridine antibacterial/antifungal agent is dispersed. In addition, even if various other treating agents such as a dye and a softener are used together in processing the fibers, and if these treating agents contain cations or anions, the pyridine antibacterial/antifungal agent is kept appropriately dispersed, without foaming. This means that there are no longer restrictions on the types of usable dyes, softeners and various other treating agents, and it is now possible, by using the above-described antibacterial/antifungal properties-imparting agent, to appropriately perform a process of imparting antibacterial/antifungal properties to fibers together with other processes using other treating agents.

DESCRIPTION OF EMBODIMENTS

Next, antibacterial/antifungal properties-imparting agents, fiber processing agents and methods for producing antibacterial/antifungal fibers according to embodiments of the present invention will be described specifically. It should be noted here that antibacterial/antifungal properties-imparting agents, fiber processing agents and methods for producing antibacterial/antifungal fibers according to the present invention are not limited to those which will be described hereinafter, but may be varied as appropriately within the scope of the invention.

In the antibacterial/antifungal properties-imparting agent according to the present invention, the pyridine antibacterial/antifungal agent can be provided by a pyridine compound such as 2-chloro-6-trichloromethyl pyridine, 2-chloro-4-trichloromethyl-6-methoxy pyridine, 2-chloro-4-trichloromethyl-6-(2-furylmethoxy)pyridine, di-(4-chlorophenyl)pyridyl-methanol, 2,3,5-trichloro-4-(n-propylsulfonyl)pyridine, and zinc pyrithione. In particular, it is preferable that the pyridine antibacterial/antifungal agent is provided by zinc pyrithione for its good affinity with fibers, strong adherence to fibers which provides high wash durability, and further more, no concern that fibers will be discolored.

In the antibacterial/antifungal properties-imparting agent according to the present invention, the modified polysaccharide having reduced hydroxyl groups can be provided by polysaccharide ether, polysaccharide ester, and polysaccharide amide for example. More specific examples include: hemicellulose, gum Arabic, tragacanth gum, carrageenan, xanthan gum, guar gum, tara gum, furcellaran, tamarind seed polysaccharide, karaya gum, pectin, pullulan, gellan gum, locust bean gum, carboxymethyl cellulose (CMC), methyl cellulose (MC), ethyl cellulose (EC), hydroxymethyl cellulose (HMC), hydroxyethyl cellulose (HEC), hydroxypropyl cellulose (HPC), hydroxyethyl methyl cellulose (HEMC), hydroxyethyl ethyl cellulose (HEEC), hydroxypropyl methyl cellulose (HPMC), hydroxypropyl ethyl cellulose (HPEC), hydroxyethyl hydroxypropyl cellulose (HEHPC), slufoethyl cellulose, dihydroxypropyl cellulose (DHPC), and more. In particular, it is preferable to use cellulose ether, cellulose ester or cellulose amide for enhanced dispersion stability of the pyridine antibacterial/antifungal agent.

Also, in the antibacterial/antifungal properties-imparting agent according to the present invention, it is preferable that the wetting agent is provided by a nonionic wetting agent such as polyethylene glycol, glycerine, and polyvinyl alcohol so that the agent will not make reactions with various treating agents such as a dye and a softener even if these agents contain cations or anions.

With the above, in dispersing the pyridine antibacterial/antifungal agent in a liquid such as water when making the antibacterial/antifungal properties-imparting agent according to the present invention which contains the pyridine antibacterial/antifungal agent, a modified polysaccharide having reduced hydroxyl groups and a wetting agent, if the amount of the pyridine antibacterial/antifungal agent is small, it becomes difficult to make the dispersion liquid viscous, yet if the amount of the pyridine antibacterial/antifungal agent is too large, it becomes difficult to crush the pyridine antibacterial/antifungal agent to be dispersed. Hence, the amount of the pyridine antibacterial/antifungal agent in the antibacterial/antifungal properties-imparting agent dispersion liquid should be in the range from 5 through 50 weight %, and preferably between 10 through 40 weight %.

Also, in dispersing the pyridine antibacterial/antifungal agent in a liquid such as water, if the pyridine antibacterial/antifungal agent has a small particle size, then a longer time is necessary for, e.g., crushing the agent, and in addition, there is a concern that the crushed particles will re-aggregate. On the other hand, if the pyridine antibacterial/antifungal agent has a large particle size, then there is poor disperse stability leading to greater tendency for sedimentation because of a high specific gravity of the pyridine antibacterial/antifungal agent. Therefore, it is preferable that an average particle size of the pyridine antibacterial/antifungal agent in a dispersion liquid of the antibacterial/antifungal properties-imparting agent should be in a range from 0.1 through 1.0 μm, and more preferably between 0.3 through 0.7 μm, with the pyridine antibacterial/antifungal agent particles having a size greater than 2 μm being not exceeding 5 weight % with respect to the overall amount of the pyridine antibacterial/antifungal agent, and preferably not exceeding 3 weight %, and even more preferably not exceeding 1 weight %.

Also, in order for the antibacterial/antifungal properties-imparting agent dispersion liquid which contains a modified polysaccharide having reduced hydroxyl groups to be able to stably disperse the pyridine antibacterial/antifungal agent, it is preferable that the amount of the modified polysaccharide in the dispersion liquid should be in a range of 0.05 through 2 weight %. If the amount of the modified polysaccharide is smaller, then the pyridine antibacterial/antifungal agent is not dispersed stably, yet if the amount of the modified polysaccharide is larger on the other hand, viscosity becomes too high to stay in a liquid form, making it difficult to use.

Also, in order for the antibacterial/antifungal properties-imparting agent dispersion liquid which contains a wetting agent to be able to stably disperse the pyridine antibacterial/antifungal agent, it is preferable that the amount of the wetting agent in the dispersion liquid should be in a range of 0.5 through 10 weight %. If the amount of the wetting agent is smaller, the pyridine antibacterial/antifungal agent is not moistened sufficiently and therefore is not dispersed stably. If the amount is larger on the other hand, stability becomes poor.

According to the present invention, when manufacturing an antibacterial/antifungal fiber by using the antibacterial/antifungal properties-imparting agent dispersion liquid in which the pyridine antibacterial/antifungal agent is dispersed, a fiber is heated after the antibacterial/antifungal properties-imparting agent dispersion liquid was applied to the fiber.

Examples of the applicable fibers include those made of natural fibers such as cotton; those made of synthetic fibers such as polyester fibers, nylon fibers and polyacrylonitrile fibers; those made of semisynthetic fibers such as acetate fibers; and those made of a combination of any of these fibers. Particularly, resin fibers or synthetic fibers such as polyester fibers, nylon fibers and polyacrylonitrile fibers are more preferable. Further, among these fibers, polyester fibers provide high levels of wash durability since they have a high degree of polimarization, which allows the pyridine antibacterial/antifungal agent to strongly adhere to the fibers, with decreased leaching from the resin.

The fibers also include thread and yarn, knitted fabric, woven fabric, cloth, and various products made therefrom. Examples of the products include clothing, bedclothes, carpets and mats, curtains, interior wallcloth, and more. Particularly noticeable products are those to be used in hospitals and other medical facilities, including surgical gown, nursing gown, bed sheets, covers and other bedcloths, partitioning curtains, gauze, towels and kitchen cloth.

When applying the antibacterial/antifungal properties-imparting agent dispersion liquid to a fiber, the dispersion liquid is used at an appropriate concentration depending on the type of the fiber, purpose of the treatment, etc., so the liquid may be used at an original concentration or it may be diluted so that the pyridine antibacterial/antifungal agent has an appropriate concentration.

After the antibacterial/antifungal properties-imparting agent dispersion liquid is applied to the fiber, and when the fiber is heated, a bathing method should be employed, in which the fiber is immersed in the dispersion liquid or in the diluted liquid and is heated at temperatures of 80 through 160 degrees Celsius under an atmospheric or higher pressures. Alternatively, an in-air method may be employed, in which the dispersion liquid or a diluted liquid thereof is impregnated or applied to the fiber and then heating is performed at temperatures of 110 through 230 degrees Celsius in the air.

If the bath method is employed to impart antibacterial/antifungal properties to a fiber, one example is to use a pressure-tight container, into which the dispersion liquid or a diluted liquid thereof is added so that the pyridine antibacterial/antifungal agent will be 0.001 through 20 weight % with respect to the weight of the fiber to be processed. Then the fiber is immersed into the liquid, and heated at temperatures of 80 through 160 degrees Celsius under pressures of 0 through 620 kPa. The pressure and the temperature to be used during the heating process performed in the bath method depend upon the type of fiber to be processed. For polyester fibers, 100 through 140 degrees Celsius under pressure is preferable while 80 through 100 degrees Celsius under an atmospheric pressure is preferable for nylon, acetate and acrylic fibers, for the process. In whichever case, 30 seconds through 2 hours are enough for the processing.

If the in-air method is employed to impart antibacterial/antifungal properties to a fiber, one example is to use an open container, into which the dispersion liquid or a diluted liquid thereof is added so that the pyridine antibacterial/antifungal agent will be 0.001 through 20 weight % with respect to the weight of the fiber to be processed. Then the fiber is immersed into the liquid, or the said dispersion liquid or a diluted liquid thereof is applied to the fiber by means of spray for example. Thereafter, the fiber is taken out in the air and heated, at temperatures of 110 through 230 degrees Celsius under a dry-heat or moist-heat condition. The temperature to be used during the heating process performed in the in-air method depends upon the type of fiber to be processed. For polyester fibers, 160 through 230 degrees Celsius are desirable while 80 through 150 degrees Celsius are desirable for nylon, acetate or acrylic fibers, for the process. In whichever case, 30 seconds through 10 minutes are enough for the processing.

When imparting antibacterial/antifungal properties to a fiber using the antibacterial/antifungal properties-imparting agent dispersion liquid, there are also cases where various treating agents such as a dye and a softener are added in order to perform other processes simultaneously. According to the antibacterial/antifungal properties-imparting agent dispersion liquid, the pyridine antibacterial/antifungal agent is dispersed with the help of a modified polysaccharide having reduced hydroxyl groups, and of a wetting agent, but the liquid does not contain any surfactant. Therefore, even if the dye, the softener or other treating agents contain cations or anions, there is no chemical reaction unlike in cases where an anionic or cationic surfactant is used, so there is no aggregation, and therefore the pyridine antibacterial/antifungal agent is kept appropriately dispersed. Further, there is no foaming unlike in cases where an anionic, cationic or nonionic surfactant is added.

EXAMPLES

Next, comparison will be shown between antibacterial/antifungal properties-imparting agents according to EXAMPLES of the present invention and antibacterial/antifungal properties-imparting agents according to Comparative Examples, to demonstrate that aggregation and foaming are reduced in the antibacterial/antifungal properties-imparting agents according to the EXAMPLES when used with cationic, anionic or nonionic treating agent. It should be noted here that zinc pyrithione was used as the pyridine antibacterial/antifungal agent for the antibacterial/antifungal properties-imparting agents of the EXAMPLES and those of the Comparative Examples.

Example 1

For EXAMPLE 1. antibacterial/antifungal properties-imparting agent dispersion liquid was obtained by adding 10 weight % of zinc pyrithione (hereinafter, abbreviated as ZPT) and 1 weight % of polyethylene glycol (hereinafter, abbreviated as PEG) as a wetting agent to water, grinding the mixture with the ball mill, then adding 0.7 weight % of carboxymethyl cellulose (hereinafter, abbreviated as CMC) as a modified polysaccharide and applying 30 minutes of agitation.

Example 2

For EXAMPLE 2. antibacterial/antifungal properties-imparting agent dispersion liquid was obtained by adding 20 weight % of ZPT and 1 weight % of PEG as a wetting agent to water, grinding the mixture with the ball mill, then adding 0.5 weight % of CMC as a modified polysaccharide and applying 30 minutes of agitation.

Example 3

For EXAMPLE 3. antibacterial/antifungal properties-imparting agent dispersion liquid was obtained by adding 40 weight % of ZPT and 1 weight % of PEG as a wetting agent to water, grinding the mixture with the ball mill, then adding 0.3 weight % of CMC as a modified polysaccharide and applying 30 minutes of agitation.

Example 4

For EXAMPLE 4. antibacterial/antifungal properties-imparting agent dispersion liquid was obtained by adding 50 weight % of ZPT and 1 weight % of PEG as a wetting agent to water, grinding the mixture with the ball mill, then adding 0.3 weight % of xanthan gum as a modified polysaccharide and applying 30 minutes of agitation.

Example 5

For EXAMPLE 5. antibacterial/antifungal properties-imparting agent dispersion liquid was obtained by adding 20 weight % of ZPT and 2 weight % of PEG as a wetting agent to water, grinding the mixture with the ball mill, then adding 0.5 weight % of methyl cellulose (hereinafter, abbreviated as MC) as a modified polysaccharide and applying 30 minutes of agitation.

Example 6

For EXAMPLE 6. antibacterial/antifungal properties-imparting agent dispersion liquid was obtained by adding 20 weight % of ZPT and 3 weight % of glycerine as a wetting agent to water, grinding the mixture with the ball mill, then adding 0.3 weight % of CMC as a modified polysaccharide and applying 30 minutes of agitation.

Example 7

For EXAMPLE 7, antibacterial/antifungal properties-imparting agent dispersion liquid was obtained by adding 20 weight % of ZPT and 5 weight % of diethylene glycol monoethyl ether as a wetting agent to water, grinding the mixture with the ball mill, then adding 0.5 weight % of CMC as a modified polysaccharide and applying 30 minutes of agitation.

Example 8

For EXAMPLE 8, antibacterial/antifungal properties-imparting agent dispersion liquid was obtained by adding 40 weight % of ZPT and 3 weight % of polyvinyl alcohol (hereinafter, abbreviated as PVA) as a wetting agent to water, grinding the mixture with the ball mill, then adding 0.5 weight % of hydroxyethyl cellulose (hereinafter, abbreviated as HEC) as a modified polysaccharide and applying 30 minutes of agitation.

Example 9

For EXAMPLE 9, antibacterial/antifungal properties-imparting agent dispersion liquid was obtained by adding 40 weight % of ZPT and 3 weight % of PVA as a wetting agent to water, grinding the mixture with the ball mill, then adding 0.3 weight % of hydroxypropyl cellulose (hereinafter, abbreviated as HPC) as a modified polysaccharide and applying 30 minutes of agitation.

Comparative Example 1

For COMPARATIVE EXAMPLE 1, antibacterial/antifungal properties-imparting agent dispersion liquid was obtained by adding 20 weight % of ZPT and 3 weight % of PEG as a wetting agent to water, grinding the mixture with the ball mill, then adding 0.5 weight % of dextrin as an unmodified polysaccharide and applying 30 minutes of agitation.

Comparative Example 2

For COMPARATIVE EXAMPLE 2, antibacterial/antifungal properties-imparting agent dispersion liquid was obtained by adding 20 weight % of ZPT and 5 weight % of PEG as a wetting agent to water, grinding the mixture with the ball mill, then adding 0.2 weight % of alkylammonium hydride (manufactured by Nippon Nyukazai Co., Ltd.: Texnol L7) as a cationic surfactant and applying 30 minutes of agitation.

Comparative Example 3

For COMPARATIVE EXAMPLE 3, antibacterial/antifungal properties-imparting agent dispersion liquid was obtained by adding 20 weight % of ZPT and 5 weight % of PEG as a wetting agent to water, grinding the mixture with the ball mill, then adding 0.2 weight % of dodecyl benzene sulfonate salt (manufactured by Nippon. Nyukazai Co., Ltd.: Newcol 210) as an anionic surfactant and applying 30 minutes of agitation.

Comparative Example 4

For COMPARATIVE EXAMPLE 4, antibacterial/antifungal properties-imparting agent dispersion liquid was obtained by adding 20 weight % of ZPT and 5 weight % of PEG as a wetting agent to water, grinding the mixture with the ball mill, then adding 0.2 weight % of polyoxyalkylene alkyl ether (manufactured by Nippon Nyukazai Co., Ltd.: Newcol 2303-Y) as a nonionic surfactant and applying 30 minutes of agitation.

Comparative Example 5

For COMPARATIVE EXAMPLE 5, antibacterial/antifungal properties-imparting agent dispersion liquid was obtained by adding 20 weight % of ZPT to water, grinding the mixture with the ball mill, then adding 0.2 weight % of alkylammonium hydride (manufactured by Nippon Nyukazai Co., Ltd.: Texnol L7) which was the same as the one used in COMPARATIVE EXAMPLE 2 as a cationic surfactant and 0.5 weight % of CMC as a modified polysaccharide and applying 30 minutes of agitation.

Comparative Example 6

For COMPARATIVE EXAMPLE 6, antibacterial/antifungal properties-imparting agent dispersion liquid was obtained by adding 20 weight % of ZPT to water, grinding the mixture with the ball mill, then adding 0.2 weight % of dodecyl benzene sulfonate salt (manufactured by Nippon Nyukazai Co., Ltd.: Newcol 210) which was the same as the one used in COMPARATIVE EXAMPLE 3 as an anionic surfactant and 0.5 weight % of CMC as a modified polysaccharide and applying 30 minutes of agitation.

Comparative Example 7

For COMPARATIVE EXAMPLE 7, antibacterial/antifungal properties-imparting agent dispersion liquid was obtained by adding 20 weight % of ZPT to water, grinding the mixture with the ball mill, then adding 0.2 weight % of polyoxyalkylene alkyl ether (manufactured by Nippon Nyukazai Co., Ltd.: Newcol 2303-Y) which was the same as the one used in COMPARATIVE EXAMPLE 4 as a nonionic surfactant and 0.5 weight % of CMC as a modified polysaccharide and applying 30 minutes of agitation.

Using the antibacterial/antifungal properties-imparting agent dispersion liquids of EXAMPLES 1 through 9 and those of COMPARATIVE EXAMPLES 1 through 7, experiments were conducted to investigate aggregation in the presence of cations, anions and nonions as well as foaming.

In the experiment with cations, 100 ml of 0.1 weight % aqueous solution of benzalkonium chloride was placed in each 200-ml stoppered measuring cylinder, 10 drops of one of the antibacterial/antifungal properties-imparting agent dispersion liquids were added using a 10-ml Pasteur pipette, and, after agitation by 20 inversions for one minute, aggregation was investigated in each antibacterial/antifungal properties-imparting agent dispersion liquid. The results thereof are shown in Table 1 below.

In the experiment with anions, 100 ml of 0.1 weight % aqueous solution of dodecyl benzene sulfonate salt was placed in each 200-ml stoppered measuring cylinder, 10 drops of one of the antibacterial/antifungal properties-imparting agent dispersion liquids were added using a 10-ml Pasteur pipette, and, after agitation by 20 inversions for one minute, aggregation was investigated in each antibacterial/antifungal properties-imparting agent dispersion liquid. The results thereof are shown in Table 1 below.

In the experiment with nonions, 100 ml of 0.1 weight % aqueous solution of polyoxyalkylene alkyl ether was placed in each 200-ml stoppered measuring cylinder, 10 drops of one of the antibacterial/antifungal properties-imparting agent dispersion liquids were added using a 10-ml Pasteur pipette, and, after agitation by 20 inversions for one minute, aggregation was investigated in each antibacterial/antifungal properties-imparting agent dispersion liquid. The results thereof are shown in Table 1 below.

In the experiment about the foaming property, 100 ml of deionized water was placed in each 200-ml stoppered measuring cylinder, 10 drops of one of the antibacterial/antifungal properties-imparting agent dispersion liquids were added using a 10-ml Pasteur pipette, and, after agitation by 20 inversions for one minute, foaming was investigated in each antibacterial/antifungal properties-imparting agent dispersion liquid. The results thereof are shown in Table 1 below.

With regard to aggregation in the above experiments, cases were evaluated as "O" when aggregation did not occur in an antibacterial/antifungal properties-imparting agent dispersion liquid, and as "X" when aggregation occurred in an antibacterial/antifungal properties-imparting agent dispersion liquid. With regard to foaming, cases were evaluated as "O" when a liquid satisfied the condition that foams is 5 cm or below in height immediately after the agitation by 20 inversions and 3 cm or below after 10 minutes was satisfied. When this condition was not satisfied, cases were evaluated as "X".

In addition, bacterial resistance test conforming to JIS-L1902 was conducted using the antibacterial/antifungal properties-imparting agent dispersion liquids of EXAMPLES 1 through 9 and those of COMPARATIVE EXAMPLEs 1 through 7, with antibacterial/antifungal fibers obtained by immersing a polyester fiber (Polyester Tropical: Shikisensha Co., Ltd.) in 0.2 weight % dilution of ZPT and, after 100% wringing, heat-processing the polyester fiber commodities in the air at 190 degrees Celsius for one minute. Cases were evaluated as "O" when the antibacterial/antifungal properties were found effective, and as "X" when the antibacterial/antifungal properties were not found effective.

TABLE 1

| | Imparting Agent Ingredient & Weight Percent | | | | | | | Aggregation and Foaming | | | | |
|---|---|---|---|---|---|---|---|---|---|---|---|---|
| | ZPT | Wet Agent | | polysaccharide | | Surfactant | | Aggregation | | | | JIS |
| | Wt % | Name | Wt % | Name | Wt % | Type | Wt % | Cation | Anion | Nonion | Foam | Test[5] |
| E1 | 10 | PEG | 1 | CMC | 0.7 | — | — | O | O | O | O | O |
| E2 | 20 | PEG | 1 | CMC | 0.5 | — | — | O | O | O | O | O |
| E3 | 40 | PEG | 1 | CMC | 0.3 | — | — | O | O | O | O | O |
| E4 | 50 | PEG | 1 | Xan[3] | 0.3 | — | — | O | O | O | O | O |

TABLE 1-continued

| | Imparting Agent Ingredient & Weight Percent | | | | | | | Aggregation and Foaming | | | | |
|---|---|---|---|---|---|---|---|---|---|---|---|---|
| | ZPT | Wet Agent | | polysaccharide | | Surfactant | | Aggregation | | | | JIS |
| | Wt % | Name | Wt % | Name | Wt % | Type | Wt % | Cation | Anion | Nonion | Foam | Test[5] |
| E5 | 20 | PEG | 2 | MC | 0.5 | — | — | ○ | ○ | ○ | ○ | ○ |
| E6 | 20 | Gly[1] | 3 | CMC | 0.3 | — | — | ○ | ○ | ○ | ○ | ○ |
| E7 | 20 | DiE[2] | 5 | CMC | 0.5 | — | — | ○ | ○ | ○ | ○ | ○ |
| E8 | 40 | PVA | 3 | HEC | 0.5 | — | — | ○ | ○ | ○ | ○ | ○ |
| E9 | 40 | PVA | 3 | HPC | 0.3 | — | — | ○ | ○ | ○ | ○ | ○ |
| C1 | 20 | PEG | 2 | Dex[4] | 0.5 | — | — | x | ○ | ○ | ○ | ○ |
| C2 | 20 | PEG | 5 | — | — | Cationic | 0.2 | ○ | x | ○ | x | ○ |
| C3 | 20 | PEG | 5 | — | — | Anionic | 0.2 | x | ○ | ○ | x | ○ |
| C4 | 20 | PEG | 5 | — | — | Nonionic | 0.2 | ○ | ○ | ○ | x | ○ |
| C5 | 20 | — | — | CMC | 0.5 | Cationic | 0.2 | ○ | x | ○ | x | ○ |
| C6 | 20 | — | — | CMC | 0.5 | Anionic | 0.2 | x | ○ | ○ | x | ○ |
| C7 | 20 | — | — | CMC | 0.5 | Nonionic | 0.2 | ○ | ○ | ○ | x | ○ |

E1-E9: EXAMPLES 1-9
C1-C7: COMPARATIVE EXAMPLES 1-7
Gly[1]: Glycerine
DiE[2]: Diethylene Glycol Monoethyl Ether
Xan[3]: Xanthan Gum
Dex[4]: Dextrin (Unmodified)
JIS Test[5]: Bacterial resistance test It was found from the results that, in the antibacterial/antifungal properties-imparting agent dispersion liquids of EXAMPLES 1 through 9 which were prepared by adding a modified polysaccharide having reduced hydroxyl groups and a wetting agent to zinc pyrithione provided as a pyridine antibacterial/antifungal agent, no aggregation or foaming occurred in the presence of cations, anions or nonions. This demonstrates that, in the antibacterial/antifungal properties-imparting agent dispersion liquids of the EXAMPLES, the pyridine antibacterial/antifungal agent will remain properly dispersed, and will not cause foaming even when cations or anions are contained in various treating agents such as dyes and softeners. Hence, there no longer are restrictions on the types of treating agents such as dyes and softeners that can be used, and it is now possible that processes of imparting antibacterial/antifungal properties to fiber commodities are properly performed simultaneously with other processes using various treating agents.

In contrast to this, aggregation occurred in the antibacterial/antifungal properties-imparting agent dispersion liquid of COMPARATIVE EXAMPLE 1 which was obtained by adding dextrin as an unmodified polysaccharide to zinc pyrithione provided as the pyridine antibacterial/antifungal agent, under the presence of cations.

Further, aggregation and foaming occurred in the antibacterial/antifungal properties-imparting agent dispersion liquids of COMPARATIVE EXAMPLEs 2 and 5 which contained a cationic surfactant in place of a modified polysaccharide having reduced hydroxyl groups or a wetting agent, under the presence of anions. Aggregation and foaming also occurred in the antibacterial/antifungal properties-imparting agent dispersion liquids of COMPARATIVE EXAMPLEs 3 and 6 which contained an anionic surfactant in place of a modified polysaccharide having reduced hydroxyl groups or a wetting agent, under the presence of cations. No aggregation but foaming occurred in the antibacterial/antifungal properties-imparting agent dispersion liquids of COMPARATIVE EXAMPLEs 4 and 7 which contained a nonionic surfactant in place of a modified polysaccharide having reduced hydroxyl groups or a wetting agent.

The invention claimed is:
1. A composition consisting of:
   5 to 50 weight % pyridine antibacterial/antifungal agent dispersed in a liquid,
   a modified polysaccharide having reduced hydroxyl groups which is not a surfactant, and
   a wetting agent;
   wherein a surfactant is not present in the composition.
2. The composition according to claim 1, wherein the pyridine antibacterial/antifungal agent is zinc pyrithione.
3. The composition according to claim 1, wherein the modified polysaccharide having reduced hydroxyl groups is at least one selected from the group consisting of polysaccharide ester, polysaccharide ether and polysaccharide amide.
4. A method for processing a fiber, comprising applying the composition according to claim 1 to a fiber, and thereafter heating the fiber.
5. A method for producing an antibacterial/antifungal fiber, comprising: applying the composition according to claim 1 to a fiber; and thereafter heating the fiber.
6. A method for producing an antibacterial/antifungal fiber, comprising: soaking a fiber in the composition according to claim 1, and thereafter heating the fiber in a bath at temperatures of 80° C. through 160° C. under a normal pressure or an increased pressure.
7. The method for producing an antibacterial/antifungal fiber according to claim 5, wherein the composition is impregnated or applied to the fiber, and thereafter the fiber is heated in the air at temperatures of 110° C. through 230° C.
8. The composition according to claim 1, consisting of:
   5 to 50 weight % pyridine antibacterial/antifungal agent dispersed in a liquid,
   0.05 to 2 weight % modified polysaccharide having reduced hydroxyl groups which is not a surfactant, and
   0.5 to 10 weight % wetting agent;
   wherein a surfactant is not present in the composition.
9. The composition according to claim 8, wherein the pyridine antibacterial/antifungal agent has a particle size of 0.1 to 1.0 μm, and wherein particles having a particle size greater than 2 μm constitute 5 weight % or less of the total amount of the composition.

* * * * *